United States Patent [19]
Chien et al.

[11] Patent Number: 5,182,939
[45] Date of Patent: Feb. 2, 1993

[54] METHOD FOR DETERMINATION OF AVERAGE DOWNHOLE STEAM QUALITY BY MEASURING THE SLIP RATIO BETWEEN THE VAPOR AND LIQUID PHASES OF STEAM

[75] Inventors: Sze-Foo Chien, Houston, Tex.; Eugene F. Traverse, Denver, Colo.

[73] Assignee: Texaco Inc., White Plains, N.Y.

[21] Appl. No.: 678,092

[22] Filed: Apr. 1, 1991

[51] Int. Cl.⁵ .............................................. G01N 31/22
[52] U.S. Cl. .................................. 73/29.01; 73/861.05
[58] Field of Search ............. 73/29.01, 861.04, 861.05, 73/861.07

[56] References Cited
U.S. PATENT DOCUMENTS
4,788,848 12/1988 Hsueh ................................. 73/29.01

FOREIGN PATENT DOCUMENTS
224864 6/1958 Australia .......................... 73/861.05
1545072 9/1968 France ............................. 73/861.07
2232241 12/1990 United Kingdom ............. 73/861.07

Primary Examiner—Hezron E. Williams
Assistant Examiner—Joseph W. Roskos
Attorney, Agent, or Firm—Jack H. Park; Kenneth R. Priem; Russell J. Egan

[57] ABSTRACT

The quality of steam downhole is determined by injecting into the steam first and second tracers, each tracer having an affinity to a single of the two phases, and then sensing the passage of the tracers over a pair of sensors spaced apart or known measured distance. Thus the velocity of the phases, the slip ratio between the phases and the steam quality can be determined.

4 Claims, 1 Drawing Sheet

METHOD FOR DETERMINATION OF AVERAGE DOWNHOLE STEAM QUALITY BY MEASURING THE SLIP RATIO BETWEEN THE VAPOR AND LIQUID PHASES OF STEAM

BACKGROUND OF THE INVENTION

1. The Field of the Invention

The present invention pertains to the measurement of average downhole steam quality and in particular to the measurement of the velocity of the two phases by sensing tracers, each having a single phase affinity, over a measured distance.

2. The Prior Art

Steam flooding has become an accepted practice for recovery of petroleum products from marginal fields or reservoirs that require a degree of stimulation to produce a satisfactory flow of crude petroleum. There is a need for a simple method and apparatus to determine the quality of steam at the wellhead of an injection well. Such a measurement, if simplified, would be particularly useful in determining the amount of heat which is applied to the underground reservoir by the injected steam.

The measurement or monitoring of steam quality is important since the steam's quality and hereby its reservoir or formation heatup effect directly affects the resulting production operations. Further, the quality of the steam which can be most economically injected into a particular substrate or reservoir is contingent on a number of circumstances. The latter include the age of the reservoir and the anticipated prospects for extracting commercially justified amounts of hydrocarbon products therefrom.

In brief, it is desirable that the quality of steam which is injected into each injection well be altered or adjusted to a level of quality that best conforms to the condition of the formation penetrated by that well. Clearly the quality of the steam must be known before any alteration or adjustment can be made.

It is known that in order to be particularly effective in this type of stimulation operation, the flow of injected steam must be monitored by use of metering means positioned in the steam-carrying line adjacent the wellhead. It can be appreciated that steam will normally leave the steam generator or source at a 15 known quality, pressure and mass flow rate. As the pressurized steam flow progresses towards an injection well, however, the quality will usually be substantially decreased. A decrease in the quality can be based on such factors as the distance between the well and the source and the effectiveness of pipe insulation. It will further depend on the pipe layout including number and orientation of fittings through which the steam has to travel prior to reaching the injection port or well because of phase separation that can occur in these fittings.

It is important, therefore, as a matter of economic practicality that a flow monitoring and controlling means be instituted into the steam-carrying conduit immediately upstream of each injection wellhead. A choke mechanism in the steam line will function to constrict the steam flow to thereby allow regulation of the steam mass flow rate which enters that particular well.

U.S. Pat. No. 4,836,032 discloses the use of an orifice plate in series with a critical flow choke to provide a method of measurement for both steam quality and mass flow rate. The present invention is distinguished from this earlier invention by the fact that only the steam quality is determined. The steam quality is determined by determining the slip ratio of the average vapor phase velocity to the average liquid phase velocity. The slip ratio is a function of the steam quality.

In 1962, Vance established that the slip ratio K of steam is related to the steam quality $X°$.

$$K = \text{Slip Ratio} = \frac{\text{Average Vapor phase Velocity}}{\text{Average liquid phase Velocity}}$$

and $K = K(X°)$, Vance's data can be approximately correlated as $$K = (X°)^{-0.398}.$$

It is believed that the steam pressure could play a role in the slip ratio i.e. the exponent on the "$X°$" should be a function of a steam pressure or dimensionless pressure $$p/p_c.$$

($p_c$—critical pressure of steam = 3198.81 psia).

In a recent publication, Deichsel and Winter presented experimental data on slip ratio of critical flow of an air-water mixture and presented the slip ratio as function of quality (% of air in the mixture). Their results showed that for a quality between 10% and 100%, the slip ratio increases as the quality is reduced. They further showed that for the same quality, the slip ratio is reduced as the pressure increases. However, at a quality higher than 50%, the effect of pressure on slip ratio becomes less significant.

It should be pointed out that Deichsel and Winter's work used air and water for the two phases. There slip ratio is calculated according to an equation which showed the slip ratio as function of pipe area, density, fluid rate of the two phases and the Exit pressure and impulse force of the exit jet.

SUMMARY OF THE INVENTION

In the present invention the difference in travel time of tracers in each of the two phases of steam, known as the slip ratio, is determined. Tracers, either chemical or radioactive, having an affinity to only one phase of the steam are injected into the flowing steam. The velocity of each phase is determined by sensing the concentration of the specific tracer at two sensing stations separated by a known distance D and measuring the time interval for the tracer to travel between two stations.

BRIEF DESCRIPTION OF THE DRAWING

The present invention will be described, by way of example, with reference to the accompanying drawing, in which.

DETAILED DESCRIPTION OF THE INVENTION

Figure 1:
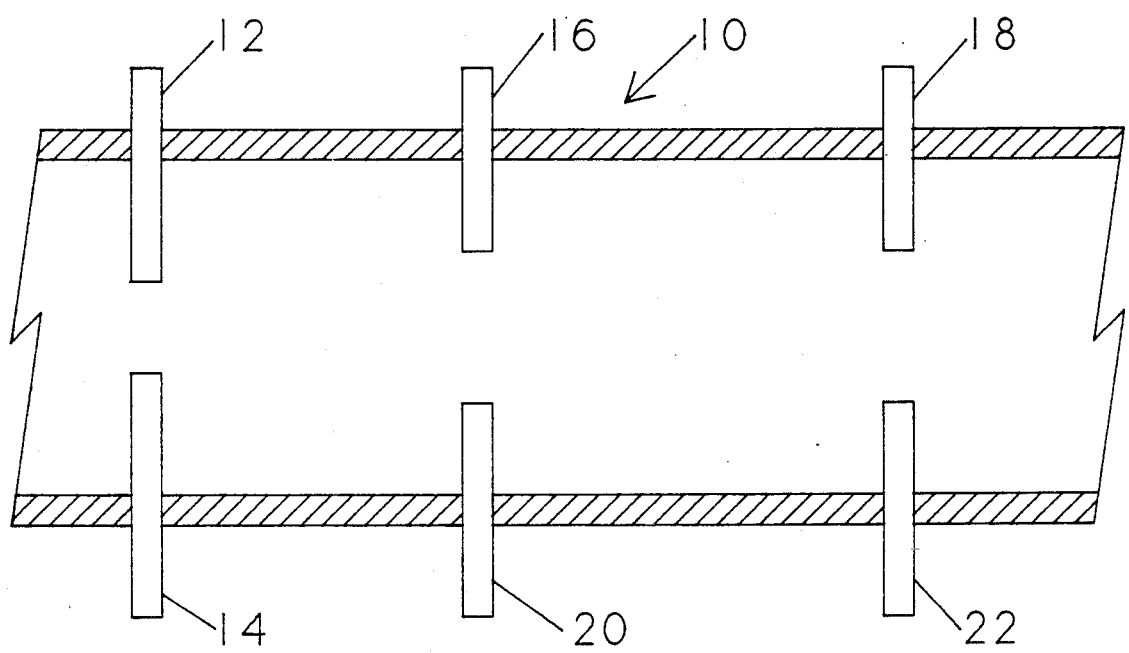
FIG. 1 is a schematic diagram of apparatus suitable for carrying out the present invention.

In order to determine the average velocity for each phase of the steam, the tracers used for the subject method must be ones that have affinity only to one of the two phases so that the travel time and the velocity of that phase can be determined. For example, Krypton 85 and sulfur hexafluoride can be used as tracers for the vapor phase of steam while thiocyanate ion and iodine ion can be used as tracers for the liquid phase of the steam. These tracers are used so that each tracer sensing device at the respective stations can determine the arrival of specific concentrations. Once the velocity of liquid and vapor phases have determined, the slip ratio can be calculated and hence the steam quality.

For any specific pressure range or flow geometry (such as pipe size), calibrations may have to be performed to establish the unique relationship between the slip ratio and the steam quality. However, the subject method can be used either for the surface steam distribution network or in the injection well.

Two methods of determining average downhole steam quality were derived based on the following information:

1. Transit times of saturated steam phases over a known interval,
2. The average pressure across the same known interval,
3. The effective volume available for steam in the same interval,
4. The mass flow rate of steam being injected. The derivations are given here for a case where the transit time of only the water phase of the saturated steam is available and for a case where both the water and vapor phase of the saturated steam is available.

To use the subject method, a tracer (such as a radioactive tracer) is introduced into the wet steam. The tracer will have an affinity for only one phase, either the liquid or vapor phase. If both phases of the steam are to be monitored, then a second tracer which has an affinity only for the other phase will also be introduced into the steam.

A suitable apparatus is schematically shown in FIG. 1. The steam line 10 (or well bore) has first and second means 12, 14 for injecting measured amounts of tracer element into the steam. The tracer elements can be radioactive or chemical tracers and each has an affinity for any one of the two phases of the steam. In this instance means 12 inserts tracer with vapor phase affinity while means 14 inserts tracer with a liquid phase affinity. Vapor tracer sensors 16, 18 are mounted in the line 10 at a measured distance apart. Likewise, liquid tracer sensors 20, 22 are mounted in the line 10 at a like measured distance.

Apparatus, such as described above, that respond to the concentration of the tracer will be located at each of several designate stations spaced known distances apart along a pipe. Each apparatus will measure tracer concentration as a function of elapsed time of arrival of the tracer at the various stations. The tracer concentration profile is related to the velocity profile of the steam phase being monitored. The velocity profile can be analyzed to determine the average velocity of the steam being monitored. An approximate transit time (the time required for the saturated steam to pass between two different stations a known distance apart) is obtained by taking equivalent points on each of the tracer concentration profiles. Either the leading edge or the midpoint of the profile can be used, as long as the choice of points is consistent.

The average pressure across the interval being monitored can be obtained by measuring the pressure or temperature at the beginning and end of the interval. If temperature is measured, the corresponding pressure for saturated steam can be obtained from the steam tables. The average pressure for the interval is defined as the arithmetic average of the two pressures. If the pressure has not been measured and the interval extends from the surface to some subsurface point, the average interval pressure can be approximated by estimating the pressure drop across the interval and subtracting one half the estimated pressure drop across the interval from the known wellhead pressure.

The effective volume available for steam in the interval being monitored is the volume down which the steam is being injected less the volume of any material which displaces steam into this same interval (i.e. wireline cable and sonde volume). This effective volume is calculated from the dimensions of the pipe or wellbore and of the steam displacing material and the interval length.

The mass flow rate of steam is a function of the steam injection rate in barrels of cold water equivalent which can be determined from the feed water supplied to the steam generator source if the total output of a single steam source is used to supply the steam to the well being monitored. In the case of steam from a common source being used to supply multiple injection wells, other means of measuring the mass steam flow rate into the subject well must be used.

The derivation of the average downhole steam quality as a function of the transit time of the water phase of the saturated steam assumes the vertical water phase acceleration was constant over all steam quality ranges. This assumes only gravity is affecting the vertical flow of the water phase and that the slippage between phases and friction are zero. In fact, slippage between the phases would increase and friction would reduce the water phase acceleration. At low steam quality the friction effect on the water phase would be at a maximum and the slippage between the phases would approach zero. At high steam quality the reverse would be true. In the mid steam quality ranges these two forces would tend to counteract each other. Because of the effect of friction and the slippage between phases in the water phase, the results from this derivation can only be used to obtain an approximation of the average downhole steam quality. However, this approximation should be good enough to indicate high, medium or low quality steam in an individual well or to compare relative steam qualities between groups of wells.

The derivation of the average downhole steam quality as a function of the transit time for both the water and vapor phases of the saturated steam assumes the total mass flow rate is the sum of the water plus vapor mass flow rates. Slippage between phases and friction do not impact this assumption and, therefore, the calculated average downhole steam quality based on this assumption will reflect the actual steam quality.

The resulting calculated steam quality is the average steam quality over the interval being monitored. This calculated average steam quality does not represent the steam quality at the midpoint of the interval being monitored because the deterioration of steam quality should accelerate with depth. This calculated steam quality should represent the steam quality at some point in the interval less than half way between the beginning and the end of the interval. The shorter the interval the closer the calculated stem quality will be to the actual steam quality at the midpoint of the interval.

If a number of intervals are monitored in a single wellbore, a steam quality versus depth profile can be constructed which would allow an approximate determination of the steam quality at any point the wellbore. The calculated steam quality obtained from each separate interval monitored is plotted at a point representing the mid-depth. The steam quality verses depth plots can be used to find steam quality at any depth of interest.

The parameters necessary for calculating downhole steam quality are:

| Field Data | Symbol | |
|---|---|---|
| Injection rate, BWPD | $W_i$ | |
| Wellhead pressure, psi | $P_{wh}$ | |
| Sonde depth, ft. | $D_s$ | |
| Tubing size, in. | $S_T$ | |
| Wireline diameter, in. | $W_D$ | |
| Sonde length, ft. | $S_L$ | |
| Sonde diameter, in. | $S_D$ | |
| Surface steam quality, fraction | $X_s$ | |
| Water tracer time, sec. | $T_f$ | |
| Leading edge | | |
| Midpoint | | |
| Gas tracer time, sec. | $T_g$ | |
| Leading edge | | |
| Midpoint | | |

| Calculated Data | Symbol | |
|---|---|---|
| Mass flow rate, lbm/sec | $\dot{m}_t$ | $= W_i (350 \text{ lbm/bbl})$ |
| Specific volume, cu. ft/lbm | | |
| Water | $v_f$ | $=$ function $P_{wh}$ |
| Vapor | $v_g$ | $=$ function of $P_{wh}$ |
| Tubing capacity, cu. ft/ft | $C_T$ | $=$ function of $S_T$ |
| Volumes, cu. ft. | | |
| Tubing | $T_v$ | $= C_T D_s$ |
| Wireline | $W_v$ | $= \dfrac{D_s \pi}{144} \left( \dfrac{W_D}{2} \right)$ |
| Sonde | $S_v$ | $= \dfrac{S_L \pi}{144} \left( \dfrac{S_D}{2} \right)^2$ |
| Effective | $V_{te}$ | $= T_v - W_v - S_v$ |

The method for calculation of steam quality when slug transit time for only the water phase is available, was derived as follows: (Steady state conditions assumed)

| | Nomenclature | | Subscripts | |
|---|---|---|---|---|
| V | = Volume, cu. ft. | f | = | Fluid (liquid water) |
| v | = Specific volume, cu. ft/lbm | g | = | Gas (steam vapor) |
| m | = Mass, lbm | t | = | Total |
| $\dot{m}$ | = Mass flow rate, lbm/sec. | z | = | Zero quality steam |
| T | = Time, sec. | te | = | effective tubing vol. |
| X | = Steam quality, fraction | | | |
| P | = Pressure, psia | | | |

Known Values
$\dot{m}_t$   measured
$T_f$   measured
P   measured
$V_{gf}$   functions of measured pressure
$V_{te}$   calculated from tubing, wireline and sonde dimensions Given:

$$\dot{m}_t = \dot{m}_f + \dot{m}_g = \frac{m_f}{T_f} + \frac{m_g}{T_g}$$

$m_f/T_f = \dot{m}_{fz}/T_{fz} = $ constant; water phase acceleration
$\dot{m}_{fz} = \dot{m}_t$
$m_t = m_f + m_g$
$\dot{m} = V/(vT)$ (V is actually $V_{te}$ if wireline and tool are accounted for)
$m = V/v$
$m + \dot{m}T$
$V_t = V_f + V_g$ -continued $$X = m_g/m_t = \frac{m_g}{m_f + m_g}$$

Derivation:

| $\dot{m}$ | = | $V/(vT)$ | ; given |
| T | = | $V/vm$ | ; rearrange |
| $T_{fz}$ | = | $V_t/v_f \dot{m}_{fz}$ | ; at zero steam quality |
| | = | $V_t/v_f m_t$ | ; substitution |
| $\dot{m}_f/T_f$ | = | $\dot{m}_t/T_{fz}$ | ; rearrange |
| | = | $T_f(v_f t/V_t)\dot{m}_t$ | ; substitution |
| | = | $T_f v_f \dot{m}_t^2/V_t$ | ; rearrange |
| $\dot{m}$ | = | $\dot{m}_f T_f$ | ; given |
| | = | $(T_f v_f \dot{m}_t^2/V_t)T_f$ | ; substitution |
| | = | $v_f T_f^2 \dot{m}_t^2/V_t$ | ; rearrange |
| $V_f$ | = | $m_f v_f$ | ; given |
| $V_g$ | = | $V_t - V_f$ | ; given |
| $M_g$ | = | $V_g/v_g$ | ; given |
| X | = | $m_g/(m_g + m_f)$ | ; given |

Procedure:
1. Solve for $m_f$ with known values of $\dot{m}_t$, $v_f$, $T_f$ and $V_t$.
2. Solve for $V_f$ with calculated $\dot{m}_f$ and known $v_f$.
3. Solve for $V_g$ with calculated $V_f$ and known $V_t$.
4. Solve for $m_g$ with calculated $V_g$ and known $v_g$.
5. Solve for X (steam quality) with calculated $m_g$ and $m_f$.

the method for calculation of steam quality when slug transit time is available for other steam phases was derived as follows. (Assumed steady state). Nomenclature and subscripts are the same as those used in the previous derivation.

Known Values:
$\dot{m}_t$   measured
$T_{fg}$   measured
P   measured
$V_{fg}$   function of measured pressure
$V_{te}$   tubing volume minus tool and wireline volumes Given:

$\dot{m}_t = \dot{m}_f + \dot{m}_g$
$m_t = m_f + m_g$
$\dot{m} = v/(vT)$ (V is actually $V_{te}$ if wireline and tool are accounted for)
$m = V/v$
$V_t = V_f + V_g$ $$X = m_g/m_t = \frac{m_g}{m_f + m_g}$$

Derivation:

| $\dot{m}$ | = | $V/(vT)$ | ; given |
| $\dot{m}_t$ | = | $\dot{m}_f + \dot{m}_g$ | ; given |
| $\dot{m}_t$ | = | $V_f/(v_f T_f) + V_g/(v_g T_g)$ | ; substitution |
| $V_t$ | = | $V_f + V_g$ | ; given |
| $\dot{m}_t$ | = | $V_f/(v_f T_f) + (V_t - V_f)/(v_g T_g)$ | ; substitution |

$\dot{m}_t(v_f T_f)(v_g T_g) = V_f v_g T_g + (V_t - V_f)(v_f T_f)$ ; multiply by $v_f T_f v_g T_g$
  $= V_f v_g T_g + V_t v_f T_f - V_f v_f T_f$ ; expand
  $= V_f(v_g T_g - v_f T_f) + V_t v_f T_f$ ; factor out $V_f$ $V_f(v_g T_g - v_f T_f) = \dot{m}_t(v_f T_f)(v_g T_g) - V_t v_f T_f$ ; rearrange
  $= (v_f T_f)(\dot{m}_t v_g T_g - V_t)$ ; factor out $(v_f T_f)$
$V_f = (v_f T_f)(\dot{m}_t v_g T_g - v_t) / (v_g T_g - v_f T_f)$ ; divide by $(v_g T_g - v_f T_f)$

| $m_f$ | = | $V_f/v_f$ | ; given |
| $V_g$ | = | $V_t - V_f$ | ; given |
| $m_g$ | = | $V_g/v_g$ | ; given |
| X | = | $\dfrac{m_g}{m_f + m_g}$ | ; given |

Procedure:
1. Solve for $V_f$ with known values of $\dot{m}_t$, $v_f$, $v_g$, $T_f$, $T_g$ and $V_t$.
2. Solve for $m_f$ with calculated $V_f$ and known $v_f$.
3. Solve for $V_g$ with calculated $V_f$ and known $V_t$.
4. Solve for $m_g$ with calculated $V_g$ and known $v_g$.

-continued

5. Solve for X(steam quality) with calculated $m_f$ and $m_g$.

The present invention may be subject to many modifications and changes without departing from the spirit or essential characteristics thereof. The present description is therefor to be considered in all respects as illustrative and not restrictive of the invention as defined in the appended claims.

We claim:

1. A method for determining the quality of two phase steam in flowing steam, said method comprising the steps of:

providing means for injecting at least two tracer materials into a steam pipe;

providing at least two pairs of spaced detecting stations in said pipe, each said pair of spaced stations being adapted to detect a specific one of said tracer materials, and said stations of each pair being spaced apart a known distance;

injecting first and second tracer materials into said steam, each said tracer material having an affinity for a respective one of said steam phases;

detecting the presence of each said tracer material as the tracer laden steam passes the respective pairs of detecting stations to determine the transit time of said tracers between the stations and the velocity of each of the two phases of the steam; and determining steam quality from the relationship of the differences between the transit time for each phase.

2. The method according to claim 1 wherein arrival time as a specific concentration of the tracer material is used to determine the travel time between the detecting stations and hence the average transit time of that phase.

3. The method according to claim 1 wherein said tracers are chemical.

4. The method according to claim 1 wherein said tracers are radioactive.

* * * * *